US010869519B2

(12) United States Patent
Barrett, Jr.

(10) Patent No.: US 10,869,519 B2
(45) Date of Patent: *Dec. 22, 2020

(54) MEMS VALVE ACTUATOR SYSTEM AND METHOD

(71) Applicant: Raymond Louis Barrett, Jr., Fort Lauderdale, FL (US)

(72) Inventor: Raymond Louis Barrett, Jr., Fort Lauderdale, FL (US)

(*) Notice: Subject to any disclaimer, the term of this patent is extended or adjusted under 35 U.S.C. 154(b) by 45 days.

This patent is subject to a terminal disclaimer.

(21) Appl. No.: 15/648,021

(22) Filed: Jul. 12, 2017

(65) Prior Publication Data

US 2017/0311668 A1 Nov. 2, 2017

Related U.S. Application Data

(62) Division of application No. 14/469,609, filed on Aug. 27, 2014, now Pat. No. 9,717,298.

(51) Int. Cl.
*A42B 3/12* (2006.01)
*F16K 31/00* (2006.01)
(Continued)

(52) U.S. Cl.
CPC .............. *A42B 3/122* (2013.01); *A42B 3/121* (2013.01); *A42B 3/281* (2013.01); *A61B 5/4064* (2013.01);
(Continued)

(58) Field of Classification Search
CPC ......... A42B 3/122; A42B 3/281; A42B 3/121; F16K 99/0048; F16K 31/004;
(Continued)

(56) References Cited

U.S. PATENT DOCUMENTS

2006/0118895 A1* 6/2006 Unger .................. B01L 3/5025
257/415
2008/0281569 A1* 11/2008 Netsch ................. G06K 9/6255
703/11
(Continued)

FOREIGN PATENT DOCUMENTS

DE 2933799 * 2/1981

*Primary Examiner* — Rene T Towa
(74) *Attorney, Agent, or Firm* — Luis Figarella

(57) ABSTRACT

A micro-electro-mechanical (MEMS) exhaust valve-based impact attenuating fluid filled cell for use in cushioning impact and decelerating of a wearer's body portion (e.g. head, shoulder, torso, etc.) after an impact. In combination with the use of accelerometers, pressure sensors, location and other electronics supply signals to a microcontroller, the controlled opening/closing of said exhaust valve (resulting in the expelling of said fluids with an optional combination with cell refill means) when certain parameters exceed a threshold. Individuals who engage in activities that carry a risk of injury to the head from impact in the normal course of the activity could, in combination with regular exams, benefit from a system that produces and updates a kinematic 3D model of the individual's head, including brain matter, cerebrospinal fluid paths, arterial and venous blood flow pathways, as well as the skull, supporting connective tissues and other biological structures in the head suitable for interaction with exogenous stimuli prepared from hypothetical or actual recorded impact events.

1 Claim, 14 Drawing Sheets

(51) Int. Cl.
*F16K 99/00* (2006.01)
*A42B 3/28* (2006.01)
*A61B 5/00* (2006.01)
*A61B 5/11* (2006.01)

(52) U.S. Cl.
CPC ........ *F16K 31/004* (2013.01); *F16K 99/0048* (2013.01); *A61B 5/002* (2013.01); *A61B 5/1114* (2013.01); *A61B 5/6803* (2013.01); *A61B 2503/10* (2013.01); *A61B 2562/0219* (2013.01); *A61B 2562/04* (2013.01); *F16K 2099/0082* (2013.01)

(58) Field of Classification Search
CPC ........... F16K 2099/0082; A61B 5/4064; A61B 2562/04; A61B 2503/10; A61B 5/6803; A61B 5/1114; A61B 5/002; A61B 2562/0219

See application file for complete search history.

(56) References Cited

U.S. PATENT DOCUMENTS

| | | | |
|---|---|---|---|
| 2011/0022369 A1* | 1/2011 | Carroll | G06N 3/02 703/11 |
| 2012/0143526 A1* | 6/2012 | Benzel | A42B 3/046 702/42 |
| 2014/0000011 A1* | 1/2014 | Johnson | A42B 3/046 2/413 |

* cited by examiner

Figure 11
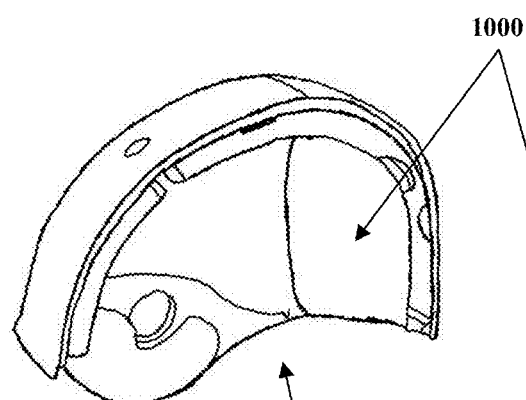
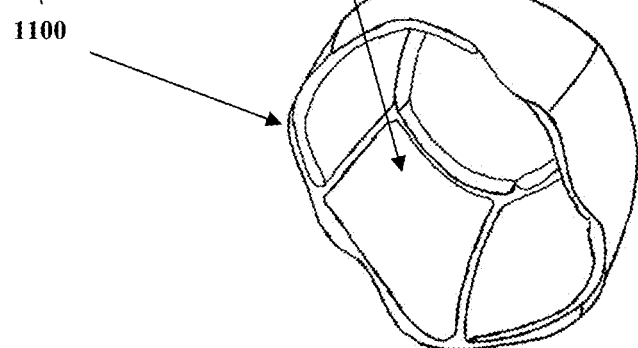
Figure 12
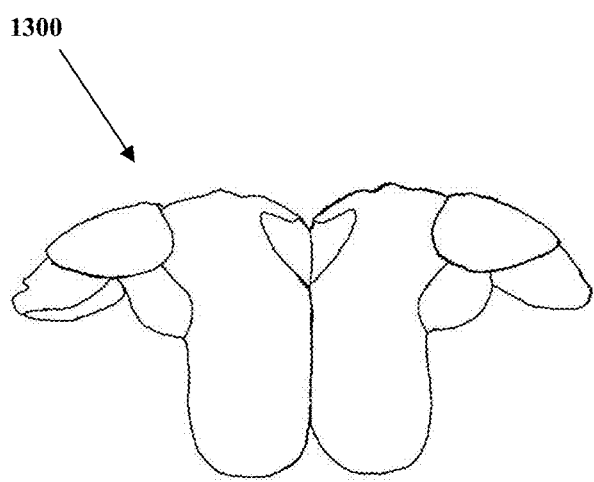
Figure 13

MEMS VALVE ACTUATOR SYSTEM AND METHOD

CROSS-REFERENCE TO RELATED APPLICATIONS

This application is a divisional of U.S. application. "MEMS VALVE ACTUATOR SYSTEM", Ser. No. 14/469,609, filed Aug. 27, 2014, the disclosure of which is incorporated herein by reference in its entirety.

CROSS-REFERENCE TO RELATED APPLICATIONS

This application claims priority to U.S. Provisional patent applications; Ser. No. 61/870,111 titled "MEMS Valve Actuator System", filed on Aug. 26, 2013; Ser. No. 61/878,008 titled "Personalized Head Model-Base System MEMS Valve Actuator System", filed on Sep. 15, 2013; Ser. No. 61/887,395 titled "Pressurized Protection Pads", filed on Oct. 6, 2013 and Ser. No. 61/896,555 titled "Impact Attenuating Pad Control System", filed on Oct. 28, 2013; the disclosures of which are herein incorporated by reference in their entirety.

PATENTS AND SUPPORTED DOCUMENTS CITED

The following patent documents and references are incorporated by reference in their entirety, D. T. Branson et al, Piezoelectric Actuation in a High Bandwidth Valve, Taylor & Francis Group LLC, Fu, Yee-Chung Ogawa et al (U.S. Pat. No. 8,383,256), Mcavoy et al (U.S. Pat. No. 8,062,612), Sanford (U.S. Pat. No. 7,106,493).

The following general documents and references are incorporated by reference in their entirety, Using Helmet Sensors in Predicting Head Kinematics, Paul Rigby, Jessica Wong, Brett Juhas, Parastou Eslami, Mark Rapo, Tim Baumer, L-3 Communications/Jaycor, 10770 Wateridge Circle, Suite 200, San Diego, Calif. 92121, Comparison of Intracranial Pressure by Lateral and Frontal Impacts—Validation of Computational Model, Aalap Patel and Tarun Goswami, Department of Biomedical, Industrial and Human Factors Engineering, Wright State University, Dayton, Ohio, USA, MODELLING OF DIRECT HEAD IMPACT INJURY MECHANISMS APPLIED TO TRANSPORT AIRCRAFT: ARE LONG PITCH SEATS SAFE?, T. H. Barth, AmSafe Aviation S. M. R. Hashemi, CIC, A. C. Walton, CIC; How can the Posit algorithm be used in head kinematic analysis? Liyi Zhao, Institutionen för informationsteknologi, Department of Information Technology; Software Tools for Dynamic and Kinematic Modeling of Human Emotion, Ernest M. Otani, University of Pennsylvania, 1989; Investigation of Brain Trauma Biomechanics in Vehicle Traffic Accidents Using Human Body Computational Models, Jikuang Yang, Research Center of Vehicle Traffic Safety/SKLVB, Hunan University, Changsha, China and Department of Applied Mechanics, Chalmers University of Technology, Gothenburg, Sweden; Mechanics of blast loading on the head models in the study of traumatic brain injury using experimental and computational approaches, S. Ganpule • A. Alai • E. Plougonven • N. Chandra, Biomech Model Mechanobiol, DOI 10.1007/s10237-012-0421-8; Design and numerical implementation of a 3-D non-linear viscoelastic constitutive model for brain tissue during impact, D. W. A. Brandsa,*, G. W. M. Petersb, P. H. M. Bovendeerdb, Department of Mechanical Engineering, Division of Computational and Experimental Mechanics, Eindhoven University of Technology, P.O. Box 513, 5600 MB Eindhoven, The Netherlands; BRAIN DEFORMATION UNDER MILD IMPACT: MAGNETIC RESONANCE IMAGING-BASED ASSESSMENT AND FINITE ELEMENT STUDY, YING CHEN, BRAD SUTTON, CHARLES CONWAY, STEVEN P. BROGLIO, AND MARTIN OSTOJA-STARZEWSKI, INTERNATIONAL JOURNAL OF NUMERICAL ANALYSIS AND MODELING, Series B Computing and Information Volume 3, Number 1, Pages 20-35; DYNAMIC RESPONSE OF HEAD UNDER VEHICLE CRASH LOADING, Mariusz Ziejewski, Ph.D. Ghodrat Karami, Ph.D., Department of Mechanical Engineering and Applied Mechanics North Dakota State University; Sports Medicine Update Newsletter, January/February 2012.

FIELD OF THE INVENTION

The present invention relates to a system utilizing miniaturized sensors and electronics to control the venting/filling of valves attached to fluid filled cells so that the acceleration effect on a human of an impact event can be controlled to provide optional peak de-acceleration. Such systems, coupled with geolocation and other signals and electronics, would allow for the use of existing medical scanning technology to prepare and track changes to various 3D models of an individual's human body (e.g. head) over time, with a sub-system for recording and reporting correlated events likely to cause impact injury to the individual, subsequent 3D models of the head following each event, and support for medical diagnoses of injuries also correlated to post-event examination.

DESCRIPTION OF THE RELATED ART

Modern systems have benefited by the propagation of miniaturization into the realms of computation, communications, and sensing, but miniaturization has been slower in progress in actuation systems. What is needed is a system for control of mechanical motions using electrical control to reap the benefits of higher response speed, shorter delays, more mechanical effect, all with the further benefits of miniaturization.

There are many activities in which a human body parts may benefit from active sensing and control of pads or cushioning cells to ameliorate the effect of impacts or other high acceleration events. From foam padding to air pads to fluid pads, many examples abound (from football helmets to explosive ordinance suits) of attempts to cushion the effect of the acceleration/deceleration felt during a high-g event.

However, many of these suffer the limitation of being a 'one-size-fits-all' solution to a problem that demands customization. Even within individuals of the same weight/height, the impact fell when falling, is different when the fall is caused by a slip that when it is accompanied by a line-backer's shoulder hit.

From fighter pilots, to race car drivers, to football players, to bomb disposal experts, the protection of the head, body core and extremities could be improved by a system capable of sensing the acceleration of felt at each individual point of impact by both the body part and the body protection article (or ground), and adjusting the rate via active measures Micro-Electro-Mechanical Systems, or MEMS, is a technology that in its most general form can be defined as miniaturized mechanical and electro-mechanical elements (i.e., devices and structures) that are made using the techniques of micro fabrication. A valve constructed with a moveable fluid-flow gating obstruction mechanism in the path of the flow and a valve-seat against which the gating obstruction approaches to obstruct the flow. When the valve gating obstruction in contact with the valve seat, the valve is defined as in its closed position. At the other end, when the valve gating obstruction is relatively far from its valve seat the valve is defined as being in its open position.

The valve governs flow through an orifice in the flow path in two asymptotic primary control regimes; regime one as the gating obstruction is nearly closed and in close proximity to the valve seat, regime two as the gating obstruction is nearly fully open and moves relatively far from the valve seat. Between these two asymptotic primary control regimes a transition behavior comprised of contributions from each regime prevails. Flow through a valve that is nearly closed is governed primarily by the area of the path defined by the valve seat perimeter multiplied by the displacement of the obstruction from the valve seat. Flow through a valve that is nearly open is governed primarily by the area of the path enclosed by the valve seat perimeter.

Various neuro-imaging technologies have been developed to scan human brains, including tracking both structural and functional characteristics. As a group, these include Computed axial tomography, diffuse optical imaging, event-related optical signals, magnetic resonance imaging, functional magnetic resonance imaging, magneto encephalography, positron emission tomography, single-photon emission computer tomography and others. The use of the above techniques is usually limited to the prediction of brain reaction to recovery from injuries and/or reaction to care protocols.

If systematically used, such personalized model can be stored and compared to later instances of that model to assist in medical diagnoses of injury from impact events. In such fashion, a collection of individual models (both 3D and kinematic), appropriately constructed from multiple technology medical scans from a collection of individuals with identity disguised, could be utilized as an ethical database reference for comparison in the causes and progression of impact injuries.

Further, the group and individual models-base could then be used in association with event/impact recordings taken in the event of a possible injury to visualize the behavior of the brain matter and fluid pressure distributions as the impact recordings are used to excite motions of the model and observe the model responses. Correlated models, event recordings, and diagnoses obtained for medical research by voluntary participation of individuals engaging in risky pursuits is an ethical means of obtaining injury-related causal linked data. The individual model can be used with a helmet system to provide a customized impact reduction intervention to ameliorate personal injury specifically tailored to that individual.

SUMMARY OF THE INVENTION

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

In one aspect the invention is about a Micro-electro-mechanical-system (MEMS) valve for selectively opening or closing a passage comprising in combination a semiconductor substrate comprised of a sandwich made from two or more piezo-electric components, a first said piezo-electric component having a set of openings going through said first component's body, a second said piezo-electric component located below said first component, said second component having a set of openings going through said component's body, said second components openings located so that when said first and second component are placed against each other there are no openings through said combined first and second component sandwich and MEMS structural components along one or more edges of one or more said piezo-electric components so that a gap between said first and said second may be opened or closed by movement of said MEMS structural components. In another aspect, said second component is comprised of one or more piezo-electric components. In yet another aspect the invention is about a method of using the above system.

In one aspect, the invention is about an active pad body part protection apparatus comprising electronic coupling components to one or more electronic control modules, a cell body defining a volume, said cell body being comprised of a flexible container formed from a fluid impermeable material, said cell body having an interior compartment for storing a fluid, and including an outer layer and an opposite inner layer, an inlet port formed in said cell body for receiving a fluid, said inlet port including a one-way valve configured to allow a fluid to be received in the interior compartment of said cell body one or more pairs of acceleration sensors attached to each said layer of said cell body, each said acceleration sensor being electronically coupled to one or more said electronic control modules, an electronically actuated MEMS valve assembly attached to said cell body, said MEMS valve in fluid communication with said interior compartment and configured to allow the control rate of the fluid venting from the interior compartment of the cell body to the exterior, said valve being electronically coupled to one or more said electronic control modules and a pressure sensor in fluid communication with said interior compartment of said cell body, said pressure sensor being electronically coupled to one or more said electronic control modules. In another aspect, the invention is about a method of using the above apparatus.

In another aspect the outer side of said cell body has a permanent shaped curvature while the inner side shape is adjusted by the pre-determined length of the inner strings or structures connecting both ends. In yet another aspect a space location component is used to establish and update the position of the apparatus above the datum or ground, and local sensors are used to establish component orientation and based on the expected point of contact of the component with said datum or ground and/or the impact from another body sensed through an accelerometer, the valve is operated as to minimize impact effects. In one aspect one or more of said apparatuses are mounted along the inside of a helmet. In another aspect one or more fluid refill components are connected to said one or more cells inlet port in order to recharge the system when fluid is expended. In yet another aspect one or more of said apparatuses are mounted along the inside of a body padding. In one aspect one or more fluid refill components are connected to said one or more cells in order to recharge the system when fluid is expended.

In one aspect, the invention is about a method for brain modeling comprising creating a model of the human brain for an individual based on kinematic/fluid dynamics data extracted from one or more brain scanning technologies and updating said model via subsequent scans after either exceptional incidents and/or regular intervals.

Other features and advantages of the present invention will become apparent upon examining the following detailed description of an embodiment thereof, taken in conjunction with the attached drawings.

BRIEF DESCRIPTION OF THE DRAWINGS

FIGS. 11-13 show illustrations of the proposed pads installed in protective equipment.

Figure 1:
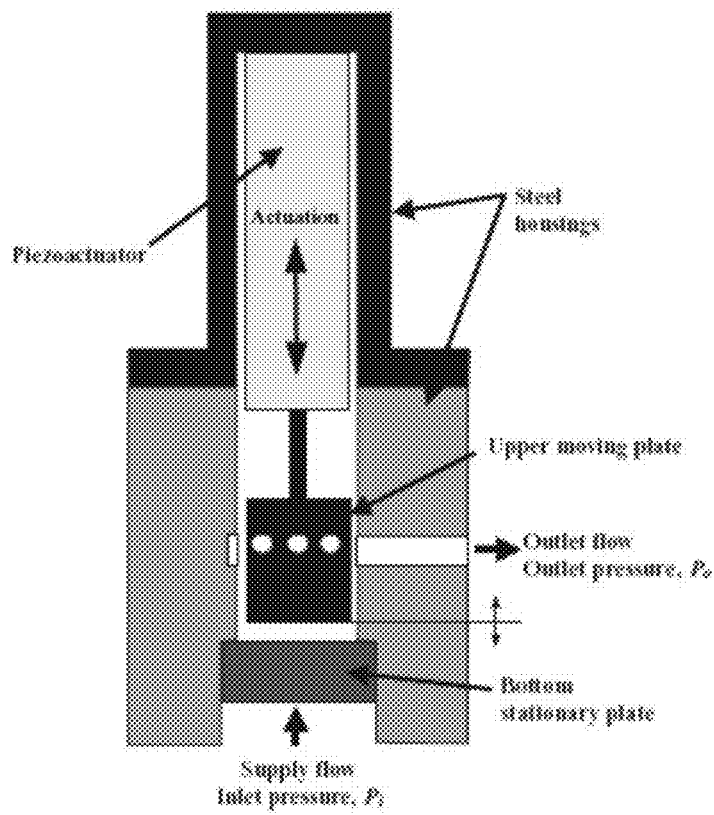
FIG. 1 shows a prior art illustration of a piston valve.
Figure 2:
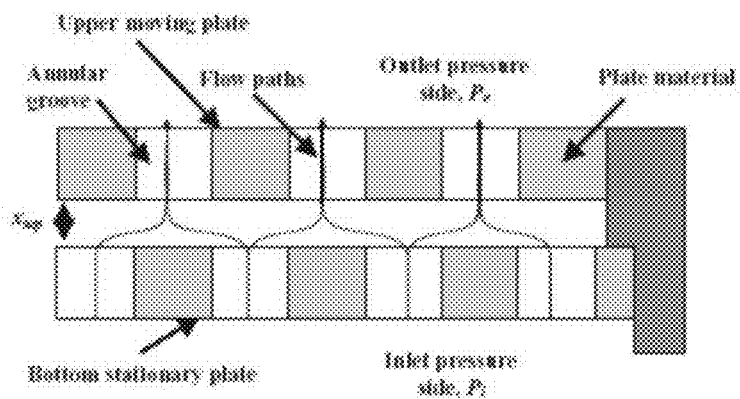
FIG. 2 shows a prior art illustration of a multi-opening/multi-path moving plate valve.
Figure 3:
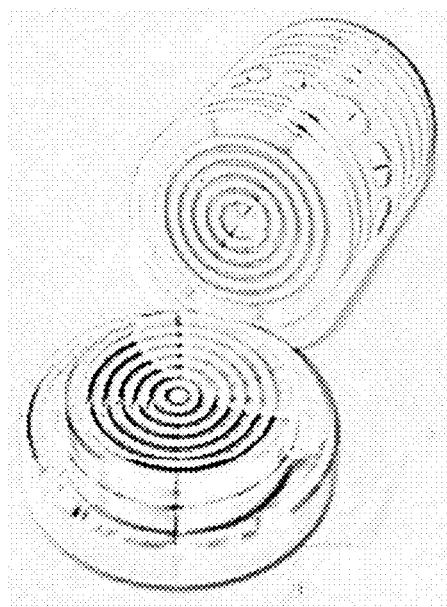
FIGS. 3-4 show prior art illustrations of valves respectively shown in FIGS. 1 and 2.
Figure 4:
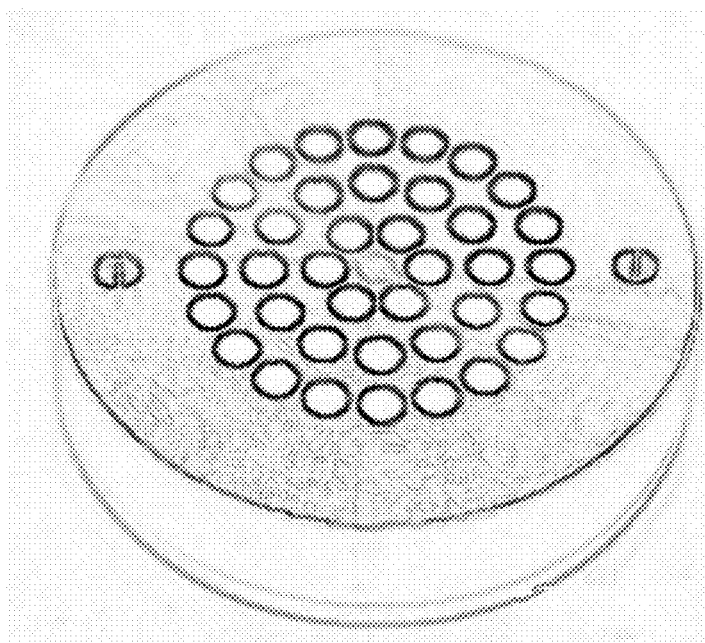

The above-described and other features will be appreciated and understood by those skilled in the art from the following detailed description, drawings, and appended claims.

DETAILED DESCRIPTION OF THE PREFERRED EMBODIMENT

To provide an overall understanding of the invention, certain illustrative embodiments and examples will now be described. However, it will be understood by one of ordinary skill in the art that the same or equivalent functions and sequences may be accomplished by different embodiments that are also intended to be encompassed within the spirit and scope of the disclosure. The compositions, apparatuses, systems and/or methods described herein may be adapted and modified as is appropriate for the application being addressed and that those described herein may be employed in other suitable applications, and that such other additions and modifications will not depart from the scope hereof.

Simplifications or omissions may be made to avoid obscuring the purpose of the section. Such simplifications or omissions are not intended to limit the scope of the present invention. All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art.

As used in the specification and claims, the singular forms "a", "an" and "the" include plural references unless the context clearly dictates otherwise. For example, the term "a transaction" may include a plurality of transaction unless the context clearly dictates otherwise. As used in the specification and claims, singular names or types referenced include variations within the family of said name unless the context clearly dictates otherwise.

Certain terminology is used in the following description for convenience only and is not limiting. The words "lower," "upper," "bottom," "top," "front," "back," "left," "right" and "sides" designate directions in the drawings to which reference is made, but are not limiting with respect to the orientation in which the modules or any assembly of them may be used.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Referring to FIGS. 1-4, an embodiment of the present invention can be easily understood when related to the operation of "large scale" valves, and then bringing them to the Micro-electro-mechanical-system (MEMS) world. A number of issues are critical when determining flow through an orifice, these include; 1) Low Pressure difference depends on the difference, 2) More than ~1 atmosphere difference "throttled" flow near speed of sound (1100 fps), 3) Downstream obstruction needs distance, 4) Resistance to flow in tubes & pipes (more open is needed/short obstructions-pipes), 5) Flow radii are obstructive, 6) Short, multiple paths through obstructions. In contrast, Valve Lift depends on 1) Seat Perimeter, 2) Lift height, 3) Lift velocity (shorter distance), 4) Valve moving masses (F=ma), 5) Discrete seat perimeter for higher sealing forces.

Piezo actuation depends on 1) Cantilever—built into spring elements Longer lift distance, less available force and slower resulting activation, 2) Length Extension on Short distances, most force, faster. The orifice shapes themselves are important, as they are; 1) Square for simple lithography, 2) Octagon for more support at perimeter, 3) Circle for beam & drill manufacturing. The Lithographic process has 1) Semiconductor infrastructure, 2) Additional layers for Piezo & other purposes (spring constant, electrical contact, etc.)

Figure 5:
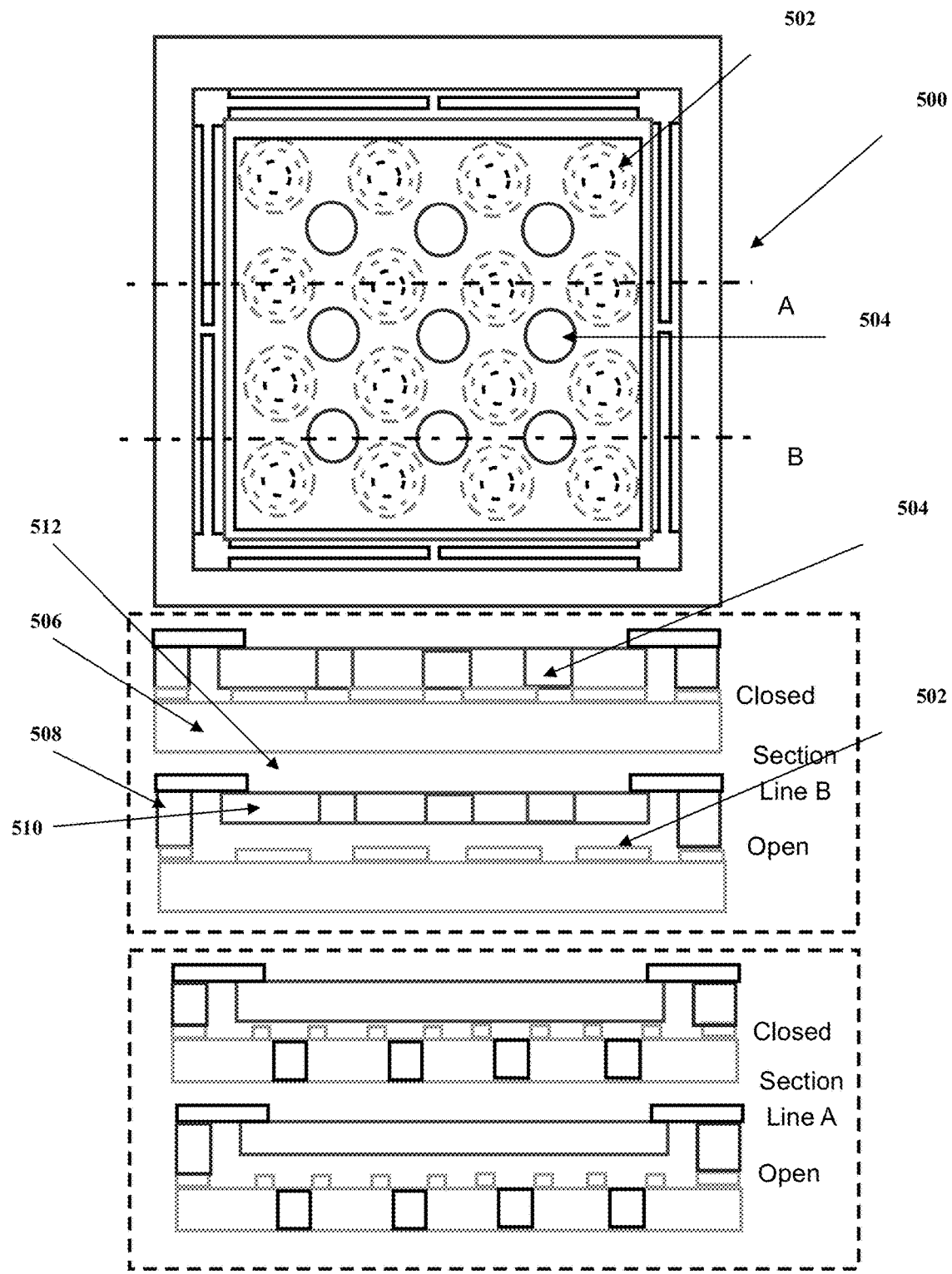
FIG. 5 illustrates a proposed Micro-electro-mechanical-system (MEMS) valve assembly, according to a proposed embodiment of the invention.
Figure 6A:
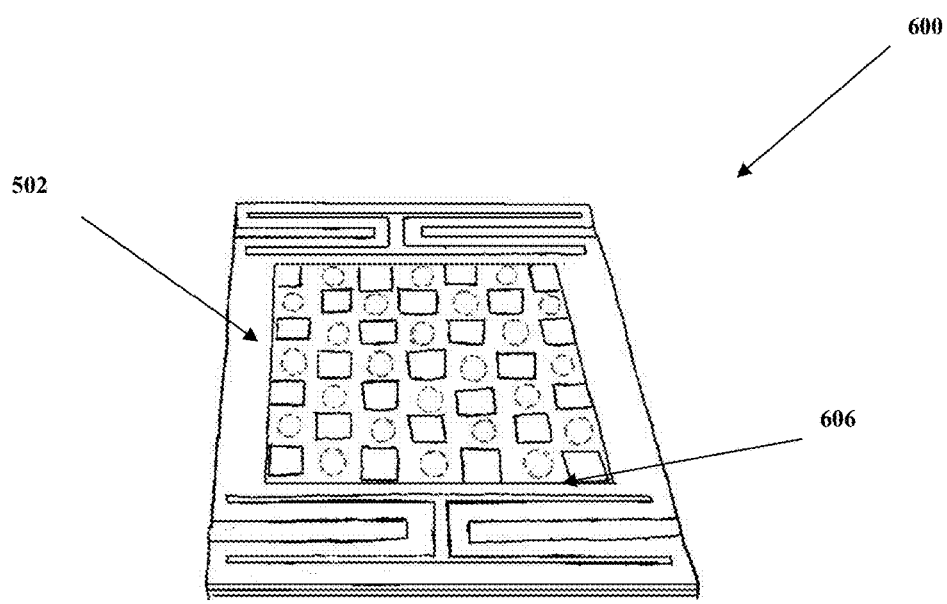
FIGS. 6A-6B show the proposed MEMS valve assembly statically, as well as in its open/close configuration, according to a proposed embodiment of the invention.
Figure 6B:
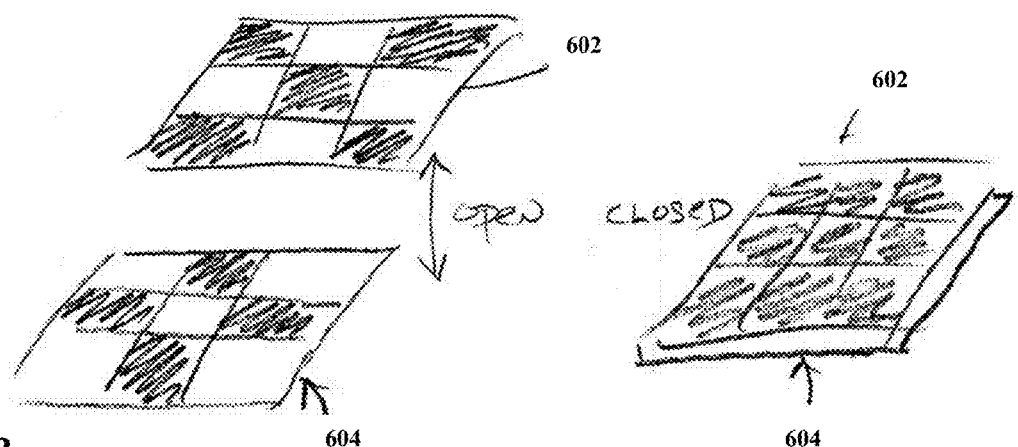

In FIGS. 5 and 6A/6B we see a proposed Micro-electro-mechanical-system (MEMS) valve that obtains good regimes when in the 1 (close) and/or 2 (open) positions. At regime-1 valve-closing control characteristics the perimeter of the valve seat is maximized. To obtain good regime-2 valve-open fluid flow rates through a valve, the area enclosed by the valve seat is maximized.

The actuator responsible for determining the position of the obstruction relative to the valve seat contributes to the control of the fluid flow. The geometry of the obstruction/valve-seat interaction sets requirements on the behavior of the actuator. Higher relative actuation speed is obtained by making the obstruction displacement between the closed and open positions as small as possible. Conversely, smaller actuation displacement translates to a requirement for long valve seat perimeter paths and large valve-seat defined areas to produce acceptable flow characteristics from closed to open states.

Of the electro-mechanical transducer families, one of the fastest approaches utilizes the piezoelectric characteristics of selected materials and is the preferred approach for miniaturized actuator applications. To reap the benefits of piezoelectric actuation, the entire valve mechanism must be constructed using minimum moving masses as well as minimum valve actuation displacement. Fortunately, the extension property of classes of some piezoelectric materials provides fast mechanical responses with relatively small displacements appropriate for actuator service.

Combining the requirement for large-area valve-seat structures with long valve-seat perimeter introduces complicated valve-seat aperture shapes that are most easily manufactured using photo-lithography and/or 3D printing technologies as the preferred implementation technologies. The piezoelectric materials selection is more limited than the material selection for the valve-seat and obstruction so that the valve aperture combination is presently implemented in different materials and the valve/actuator subassemblies co-joined in the manufacturing operation although this is a limitation of present materials selection rather than fundamental to the approach.

We see an embodiment of the MEMS valve 500. Wherein we see the valve in open and close positions, represented by the lowering or joining of the two portions, with the fluid flow 512 being shown when open. The two portions may be opened in a number of ways. In one embodiment, it is done when the edge piezoelectric component 508 expands or contracts under voltage control. Similarly, the additional piezo electric portions 510 may be used alone or in combination. When closed, the fluid is inhibited from moving. When open, the fluid starts in one end, goes through the one opening 504, across the gap between parts and exits through the other side openings 502.

In an alternate embodiment, the valve opposite sides 602, 604 have complementary openings, and one or more MEMS springs 606 using lithography techniques are used to join or separate them. These shapes are critical, allowing for low profile valves that may be controlled finitely.

Figure 7:
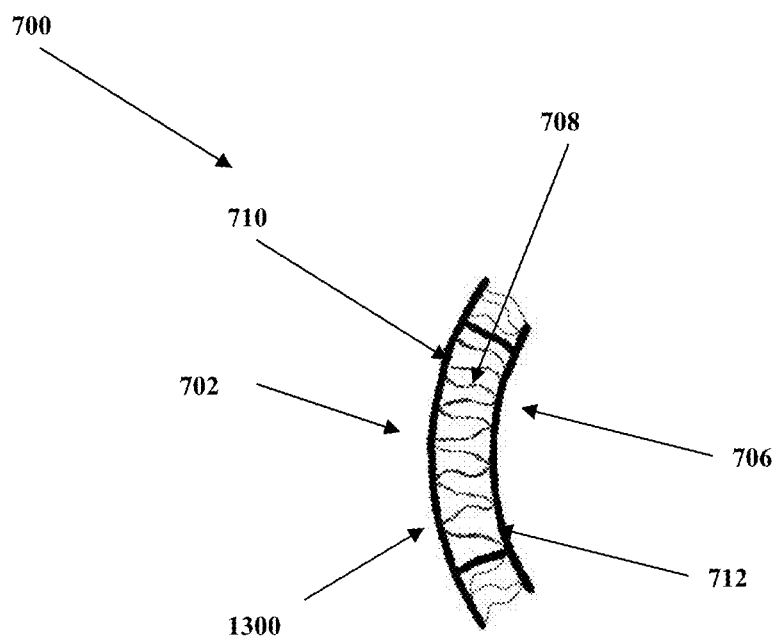
FIGS. 7-9 illustrate proposed pad micro-structure components and structural elements, according to proposed embodiments of the invention.

Referring to FIG. 7, we see a basic illustration of a pad structure to create a lightweight, fluid-filled, valve-pressure limited suspension system that ameliorates high acceleration events by holding the peak pressure to a limited value. The pressure-relief valve (which may be a MEMS valve) controlled suspension system shown four major component sub-systems; suspended object 706 (protected by the rigid enclosure), rigid enclosure structure 702, one or more pressurized pad 704, and one or more pressure-relief valve controls to control the pressure within the inside 708 of said pad 704.

A particular feature of the pad structure 700 is the ability to have permanent curvatures in its shape, so that the outer side 710 has a permanent shaped curvature (to fit a solid structure that lays against something 'standard' like a helmet or body armor), while having an inner side 712 which may be softer/foldable (say against a person's head or body), and even tailored in inner shape by adjusting the length of the inner strings or structures 800.

Such a light-weight, fluid-filled, actively controlled suspension system would ameliorate high acceleration events by holding peak acceleration, velocity, and displacement trajectories to pre-determined behaviors. Insofar as the suspension system provides support, it is called upon to be efficacious without adding excessive cost, weight, or risks in operation. What is disclosed is a light-weight, fluid-filled, actively limited suspension system that ameliorates high acceleration events by holding the peak pressure to a limited value. An electronic controller for a light-weight, fluid-filled, actively controlled suspension system that ameliorates high acceleration events by controlling the peak acceleration, velocity, and displacement trajectory is disclosed.

Using the above, a Valve-Pressure Limited Pressurized Suspension System, Improved Active Damping Pressurized Suspension System, Actively Limited Pressurized Suspension System, Active Damping Pressurized Suspension System, Active Damping Suspension Pad Controller System, Helmet Surface Kinematic Model System, Active Damping Suspension Helmet Controller System, Active Damping Suspension Model Reference Helmet Controller System, Helmet Collision Event Amelioration System.

In effect, we can control the pressure maintained within the cavity via the controlled actuation of a MEMS valve. If we equip the unit with an accelerometer (or control said valve based on the input from an accelerometer whose location can be related to the cavity or pad), we can then integrate said acceleration to establish velocity, and further integrate said velocity to establish the unit's position. Thus, a player having said pad on his/her body and/or helmet would have a pad that would be able to adapt its pressure (via control of the MEMS valve and/or any refilling means through said valve or nearby openings).

Thus the system can use the position/velocity/acceleration information to calculate, regulate and control said pressure to meet and maintain a minimum or maximum acceleration within certain distance limits. In this sense, it is not a "peak acceleration limit", but one that ameliorates smaller acceleration events to prevent repeated "peak" events. Such a system, would be superior to a simple pressure relief valve system.

In one embodiment, the system is a contact sport head protection pad within a helmet in a stadium application. A navigation or space location component (e.g. Local triangulation, GPS or differential GPS) is used so establish the position of the player above the datum or ground, and local sensors are used to establish player orientation. It is the acceleration directly that is controlled with unknown "mass" in Newton's equations, so the use of said accelerometers further establishes velocity and position. When the player is away from the ground, the system refrains from using all of it's shock absorbing, but when the head is known to be making contact with the ground, all energy is expended. The above prevents both only "compressive" accelerations (where the system is not "sticky" and cannot decelerate the other direction), as well as by its structural limitation prevents the unit from a "balloon" expansion.

Also, the surfaces can have some curvatures, convex on one side, concave on the other by varying surface parameters (thickness, shear compliances, etc.) as well as the distribution of supporting tensile members. {think of a structure of tetrahedral as in finite element meshes, but with differing triangle surfaces inner/outer) The hex-cell is an embodiment of a tensile spacer, but there are others . . . .

In one embodiment, electronically controlled means for support and positioning of an object that ameliorates the effects of impacts and other events that might otherwise damage the object being supported without adding excessive cost, weight, or risks in operation. Using pressure-relief valve controlled means for support and positioning of an object, ameliorates the effects of impacts and other events that might otherwise damage the object being supported without adding excessive cost, weight, or risks in operation.

A helmet suspension system using a pressurized fluid suspension that is designed to support and position the head without damage to the head or the support system despite enduring impacts, drops, and other events or mishaps occurring either normally or by accident requires a source of high pressure fluid to recharge. Following an event that vents fluid from the pad, the volume of fluid must be replenished to ensure proper operation for ensuing events. It is inconvenient to require the wearer of the helmet to return to a recharging location to refill each pad. What is needed is a light-weight, fluid-filled pad suspension fluid reservoir and recharging manifold to ensure each pad is promptly refilled following each venting event.

In one embodiment, such a pressurized fluid suspension system for support and positioning of a head within a helmet would ameliorate the effects of impacts and other events that might otherwise damage the head being supported without adding excessive cost, weight, or risks in operation. A fundamental premise of such a pressurized suspension pad is that the object inside an enclosure can be suspended using the pressure in the pad devices to reduce or eliminate the risk of an excessive impact. A reservoir is provided and a pressure regulation valve is added to reduce the reservoir pressure to near the requisite pre-charge pressure prescribed for the pressurized fluid suspension pads. A distribution manifold and individual pad charging valves are included so that individual pads can be changed for testing and replacement.

A fundamental premise of the actively controlled suspension system is that the object inside an enclosure can be suspended using the pressure in the pad devices to reduce or eliminate the risk of an excessive impact. A fundamental premise of the pressure-relief valve controlled suspension system is that the object inside an enclosure can be suspended using the pressure in the pad devices to reduce or eliminate the risk of an excessive impact. The pressurized actively controlled suspension system allows for the object inside an enclosure to be suspended using the pressure in the pad devices to reduce or eliminate the risk of an excessive impact, allowing a kinematic suspension model to be developed so that specifications and limits can be produced from the expected behaviors.

Using miniaturized sensors, accelerations can be utilized to calculate relative locations for the center-of-mass for the helmet and the head. Both relative translation and rotation behaviors are calculated from the same sensor trajectories and the relative motions reported as evidence of collisions and/or used for active control targets for collision effect amelioration. Using differential accelerometers, the separation distance between the helmet and the suspended head, the velocity trajectories, as well as acceleration trajectories can be combined to calculate the relative motion of the head with respect to the helmet and set trajectory targets without exceeding the suspension travel limits.

Using miniaturized sensors and controllable venting valves, an impact event acceleration can be controlled to provide maximum peak acceleration. Using individually controlled suspension pads separation distance between the helmet and the suspended head, its velocity trajectory, as well as acceleration trajectory can be controlled to ensure the support is provided without exceeding the suspension travel limits.

Insofar as the suspension system provides support, it is called upon to be efficacious without adding excessive cost, weight, or risks in operation. An electronic controller for a light-weight, fluid-filled, actively controlled suspension system that ameliorates high acceleration events by controlling the peak acceleration, velocity, and displacement trajectory is disclosed. Combining the information from the collection of pads located around the head permits identification of a kinematic model of the head's motion within the helmet.

Use of that model as a reference permits further amelioration of impact and rotation effects by treating the ensemble of pad controller objectives as a coherent set to further reduce undesirable impact effects. What is disclosed is a light-weight, fluid-filled, actively controlled suspension system that ameliorates high acceleration events by holding peak acceleration, velocity, and displacement trajectories to pre-determined behaviors while calculating the relative positions of the head and the helmet center-of-mass and center-of-rotation with respect to each other.

In one embodiment, augmenting the information to the controller with a GPS derived position signal permits calculation of the height of the head from a ground datum reference and establishment of a predictive limit for free-fall control of an unconscious helmet wearer. In another embodiment, an electronically controller means for support and positioning of a head within a helmet that ameliorates the effects of impacts and other events that might otherwise damage the object being supported without adding excessive cost, weight, or risks in operation.

In one embodiment, an electronically controller means for support and positioning of a head within a helmet ameliorates the effects of impacts and other events that might otherwise damage the object being supported without adding excessive cost, weight, or risks in operation. A kinematic suspension model may be developed so that specifications and limits can be produced from the expected behaviors.

In one embodiment, mechanical structures are constructed using components that result in load stress concentrations at the exterior surfaces. Notably, many materials that may be selected to comprise the external surfaces are able to support tensile stress or compressive stress without breakage in various ratios. Likewise, such materials are characterized by their weight and an important characteristic is their strength-to-weight ratio. Some synthetic fibers, as well as notable insect fiber materials, possess remarkably high tensile strength to weight ratios. Because these remarkably strong materials do not support compressive loads, what is needed is a means for constructing load-bearing components that utilize the tensile properties of select materials and avoid compressive stress despite possibly supporting compressive loads by the component.

Figure 8:
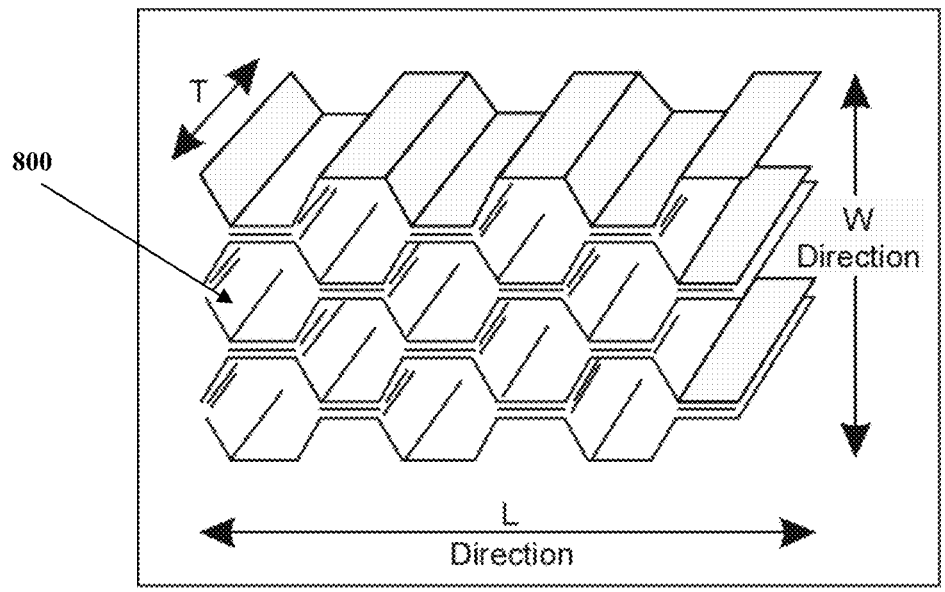

The present invention relates to a means for constructing a composite structure of external surfaces with a high-tensile material that constrains the separation of said external surfaces permitting construction of a volume-enclosing shape with all external surfaces pre-loaded into tensile stress and resulting in a tensile stress in the separator material also to maintain that shape. As seen in FIG. 8, such a high tensile "Honeycomb" Fabric Separator Material" could be embodied from a high-tensile material suitable for a separator. Such a unit would be comprised of multiple layers of porous fabric woven from high-tensile fibers are combined, one set of fibers in the weave are aligned straight along the T dimension, an adhesive is applied in strips to the alternate layers of the fabric, alternate layers are offset so that adhesive strips do not overlap, adhesive is cured, joining the alternated layers, and said layers may be stretched showing the honeycomb appearance.

Figure 9:
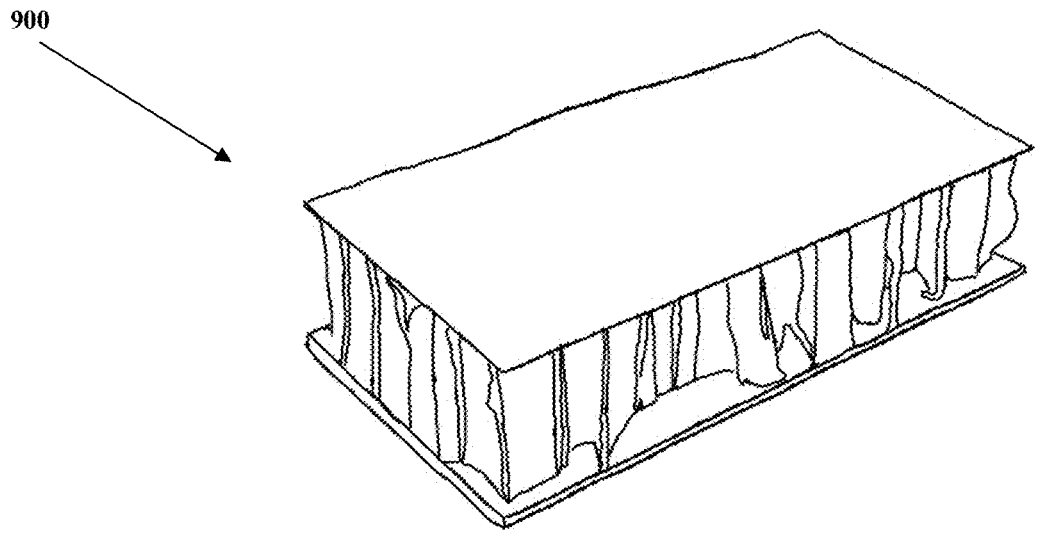

Such a separator material may be used to construct numerous useful structures as illustrated by an application to a parallel-plate panel 900 shown in FIG. 9 as one embodiment. A High-Tensile Separator Parallel-Plate Panel can be constructed using an inner and outer semi-rigid flexible surface material impervious to fluid flow, high-tensile honey-comb separator between the surfaces that relatively limits the maximum separation of the surfaces, relatively does not limit the minimum separation of the surfaces, and permits fluid flow between and parallel to the surfaces. In addition, a perimeter semi-rigid surface (not shown) to enclose a volume of fluid, and an adhesion of the honey-comb to the surrounding semi-rigid surfaces.

Introduction of a fluid into the empty bounded space increases that volume with relatively little increase in pressure up to a bounding volume. At the maximum bounding volume, the pressure increases rapidly with little increase in volume as fluid is added. All external surfaces, upper, lower, and perimeter, as well as the separator material are placed in tensile stress by the difference in internal and external fluid pressures. External compressive loads on the panel result in higher internal pressure, higher tensile membrane loads and some deformation of the panel.

Figure 10:
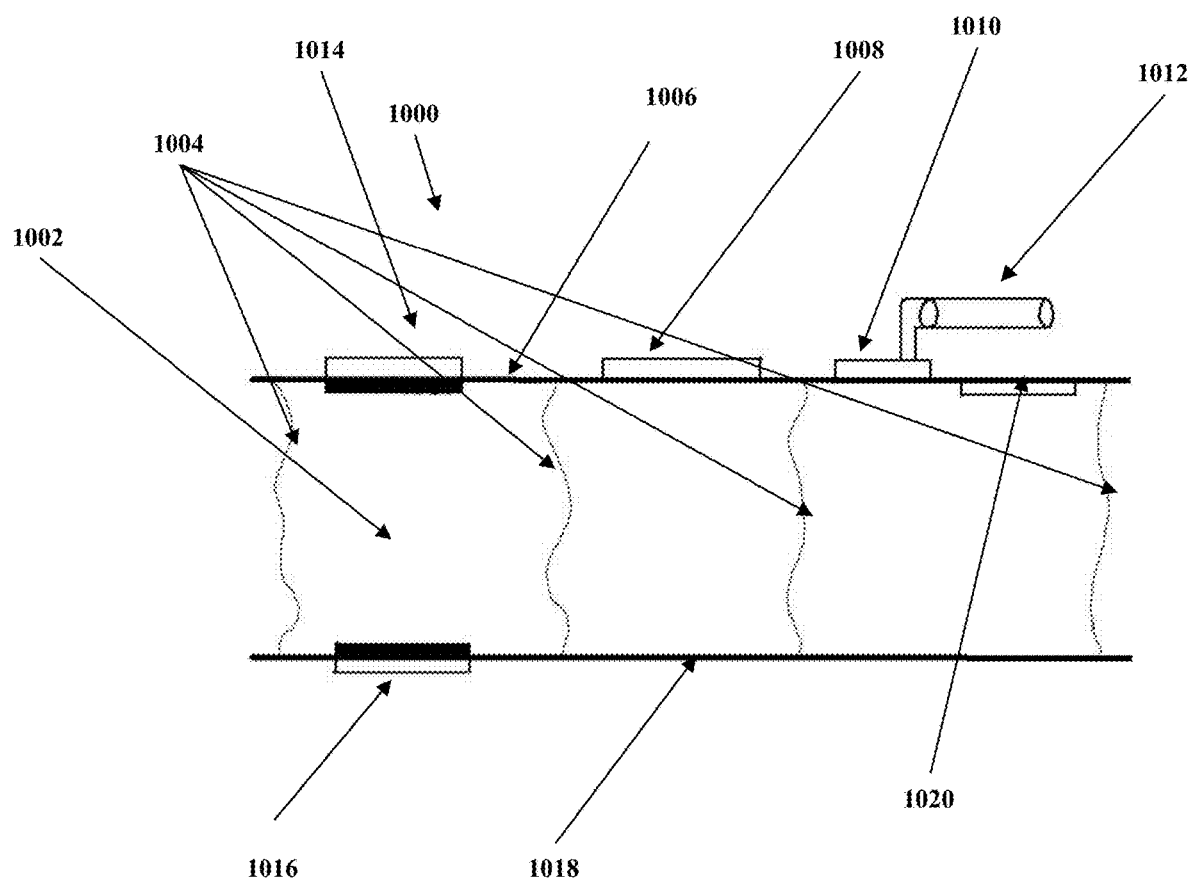
FIG. 10 shows an illustration of a proposed pad, according to an exemplary embodiment of the invention.

Referring to FIG. 10, we illustrate one embodiment of a proposed pad or body cell 1000 defining a volume 1002 being comprised of a flexible container envelope capable of holding a fluid within it. The fluid may be air, gas (e.g. CO, $CO_2$, Helium, etc.), water, or any combination thereof. The flexible container envelope may be formed from any combination of flexible plastics, carbon composites or other natural/manmade materials, as long as the flexibility achieved is sufficient to protect the intended target. Formed of rubber (real or synthetic), Polyester®, Nylon® (Polyamide), PAEK (polyaryletherketones), Amodel® (a semi-aromatic polyamide (PPA)), or the combination thereof of any other flexible, impermeable material would have an interior compartment or envelope 1002 for storing a fluid, including an outer layer 1006 and an opposite inner layer 1018.

A number of outlets are formed in said cell body layers (inner or outer, depending on the application). For example, a diver, pilot or astronaut may prefer the venting to be done inside towards a controlled volume, such as a diving or space suit, as long as the vents/valves clearance can be maintained. One said outlet is a refill valve 1010, which may be connectable to either an off-board refill station, or to an onboard refill unit 1012, such as a common $CO_2$ cartridge or a pyrotechnic or thermal expansion device. In this form, and under control of one or more control modules, the volume may be refilled in real-time in response to a controlled deflation, an accidental one or any other such event. The body re-charge may occur by actuation of the input valve 1010, or by activation of the refill unit 1012.

One or more pairs of acceleration sensors 1014, 1016 are attached to each said layer of said cell body (inside or outside said body volume), each said acceleration sensor being electronically coupled to said one or more electronic control modules (redundancy may be desired). One or more electronically actuated MEMS valve assembly 1008 are attached to said cell body in fluid communication with said interior compartment, configured to allow the control rate of the fluid venting from the interior compartment of the cell body to the exterior. A pressure sensor 1020 is in fluid communication with the interior volume 1002 of the cell body, as well as electronically coupled to one or more electronic control modules.

In order to prevent overpressure situations from affecting the protected body part (or component, the above system would comprise a fantastic sensitive cargo protection envelope), internal tension structures 1004 (say vanes, strings, or any other length restrictive features) could be used to ensure the volume of the cell body has a maximum length/depth.

The above and other actuators and sensors are connected through electronic coupling means to one or more electronic control modules. The control modules may be on-board or off-board, and may be comprised of micro-controller means such as microprocessors, Field Programmable gate arrays (FPGAs), Application Specific IC's (ASICs), complex programmable logic devices (CPLDs) or any other suitable form of electronic processing. The coupling means may be comprised of wired, flexible ICs and/or wireless links (e.g. Bluetooth or similar nets) or any combination thereof that allows for the real-time sensing and control of the various actuators and sensors.

In an exemplary embodiment, the system works by comparing the acceleration delta between the outside 1014 and internal 1016 accelerometers. When a sensed difference in acceleration between the two accelerometers is felt, the valve 1008 is opened at a certain rate of release and/or a certain amount of time, so that the object being cushioned (say that against the inside wall 1018), does not experience the same acceleration as the outside wall 1006, (Referring to FIGS. 11-13), say the helmet 1100 or body padding 1300. Optional positioning, say that derived from a GPS receiver, or an enhanced GPS receiver using differential GPS (as inside a stadium), or even the integration of the accelerometer to generate velocity and position vectors, is used to determine the optimal deceleration.

In one example, after being activated (say because of a player being hit while airborne), location (obtained via derivation of accelerations, external input (GPS, commands), or acceleration (sensors feeling a 0-g condition or any predetermined acceptable g-load condition), may proceed to re-inflate the cell body to an acceptable condition. In this fashion, when the player/soldier who has been 'blown away' by an explosion (and protected from extreme g's by the operation of the cell body valve allowing air out), gets the cell body re-inflated while airborne and before he/she hits the ground at the end of his/her travels.

Note the above cell body may be combined with that of others to form a network of two or more cell bodies or pads forming a larger pad. For example, a helmet system may be comprised of 20 or 30 such cell bodies, whereas an arm protection module may be comprises of six or eight larger cell bodies. Power for the system electronics and other components may be obtained from on-board batteries, solar cell, super capacitors or other such sources.

As an example of the possibilities, we imagine a one-inch thick body cell designed to cushion a 100 g acceleration. The valve assembly 1008 allows substantially all of the fluid contained to discharge in order to decelerate a human skull from contacting the helmet (hence whatever the helmet is contacting) in less than 7 ms. This time estimate can be calculated using Equation 1, shown below, solving for time, t, where the distance, d, is the thickness of the cell, 1-inch, and the acceleration, a, is 100 g.

$$d=\frac{1}{2}at^2$$

The valve must fully open in a mere fraction of the 7 ms event duration to allow enough time for substantially all of the fluid to vent. If we design a 5"×4"×1" cell that contains approximately 20 cubic inches of fluid, and it can be substantially exhausted during the 7 ms event, the valve assembly must accommodate an exhaust flow rate of at least approximately 1.65 cubic feet per second, preferably at least 2 cubic feet per second. Thus, the decompression of a cell body within a few milliseconds to prevent or reduce severity and possibility of a concussion.

Figure 16:
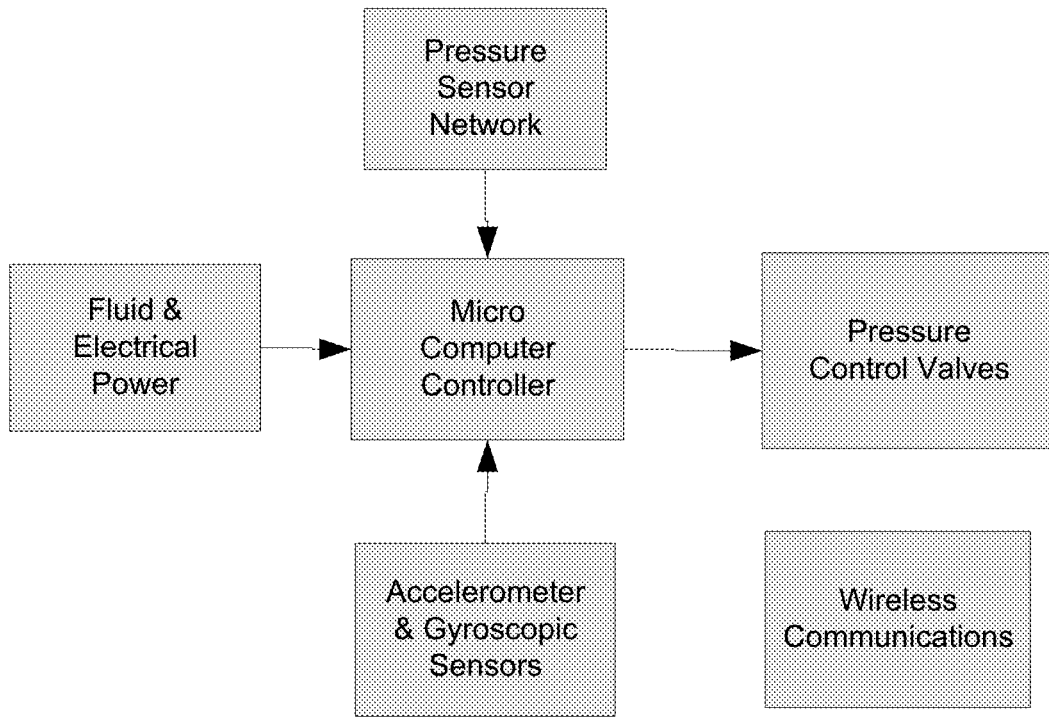
FIGS. 16-17, 18A-18C, 19A-19B, 20-23 illustrate various block diagram illustrations of the system components and their operation, according to exemplary embodiments of the invention.

In all cases listed below the canonic design includes all elements above but not all are required in every product model. Referring to FIG. 16, we see a system Block Diagram of an exemplary embodiment of a MEMS based helmet with embedded sensors and electronics that ameliorate linear and as much as possible torque impulses to reduce the occurrence of concussion events in the wearer. Ancillary objectives include data-gathering and reporting of suspect events so that diagnostic intervention can be indicated. The fundamental premise of the helmet system is that the head inside the helmet can be suspended using an active control system with suspension pad devices and the pressure distribution can be controlled in the pad devices to reduce or eliminate the risk of a concussion in the brain of the helmet wearer. The six major component sub-systems include; Fluid and Electrical Power Sub-System, Accelerometer and Gyroscopic Sensor Sub-System, Pressure Control Valves Sub-System, Pressure Sensor Network Sub-System, Micro Computer Controller Sub-System, and Wireless Communications Sub-System.

Figure 17:
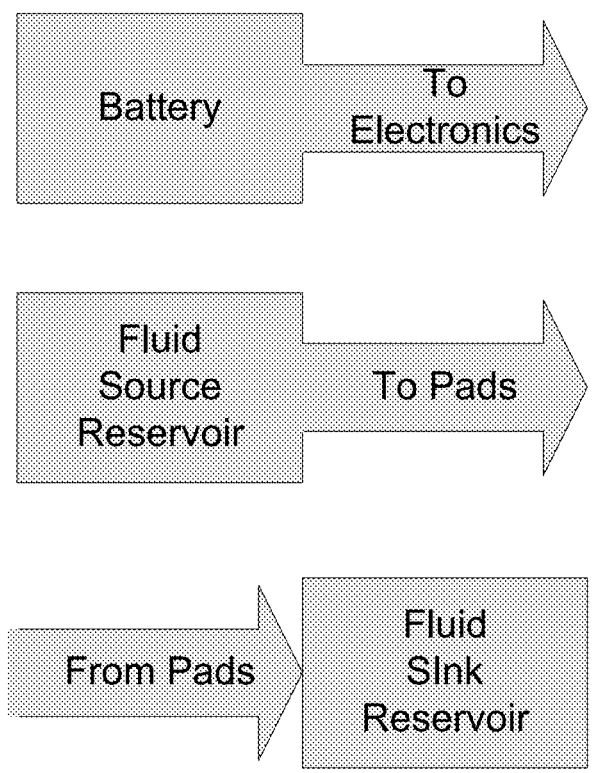
Figure 18A:
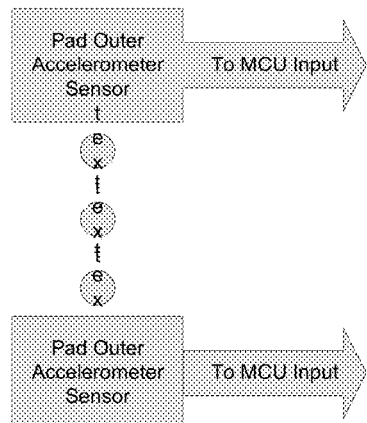
Figure 18B:
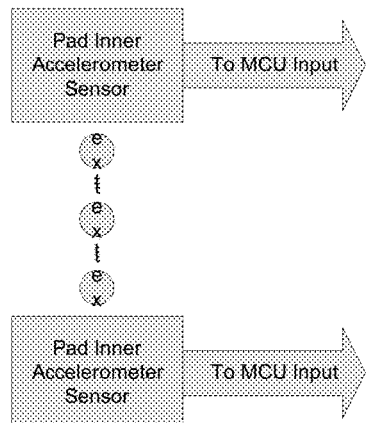
Figure 18C:
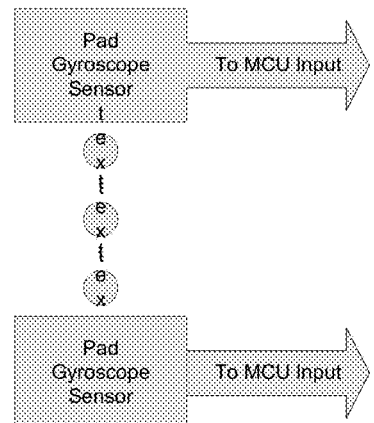

Referring to FIG. 17, we see that the Fluid and Electrical Power Sub-System Block Diagram has three major component sub-systems: An electrical battery and power conversion Sub-System, a high pressure Fluid Source Reservoir Sub-System, and a low pressure Fluid Sink Reservoir Sub-System. To illustrate the Accelerometer and Gyroscopic Sensor Sub-System Block Diagram, we note it has three major component sub-systems: a Pad Outer Accelerometer Sub-System (FIG. 18A), a Pad Inner Accelerometer Sub-System (FIG. 18B), and a Pad Gyroscopic Sub-System (FIG. 18C).

Figure 19A:
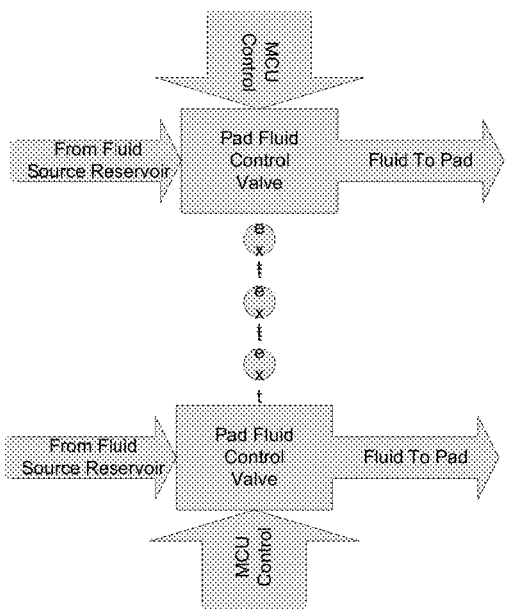
Figure 19B:
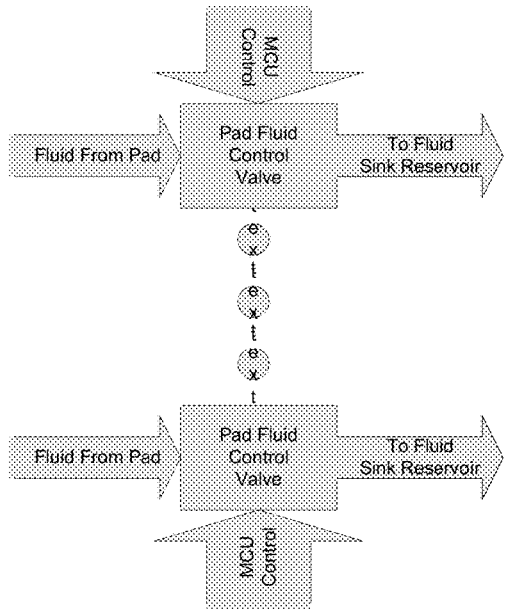
Figure 20:
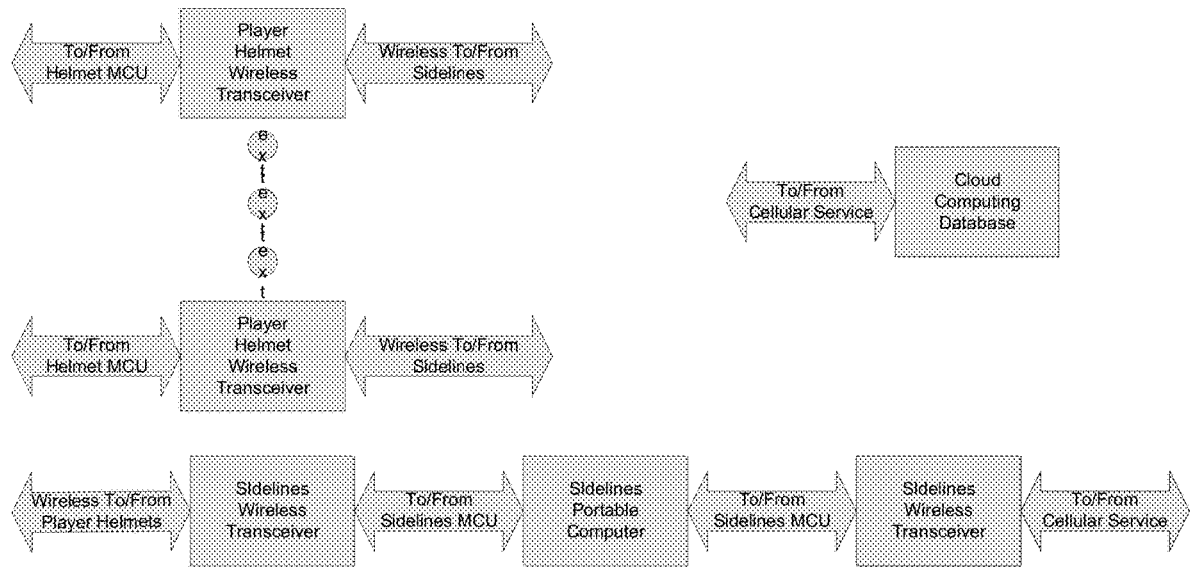
Figure 21:
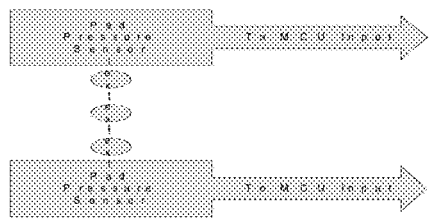
Figure 22:
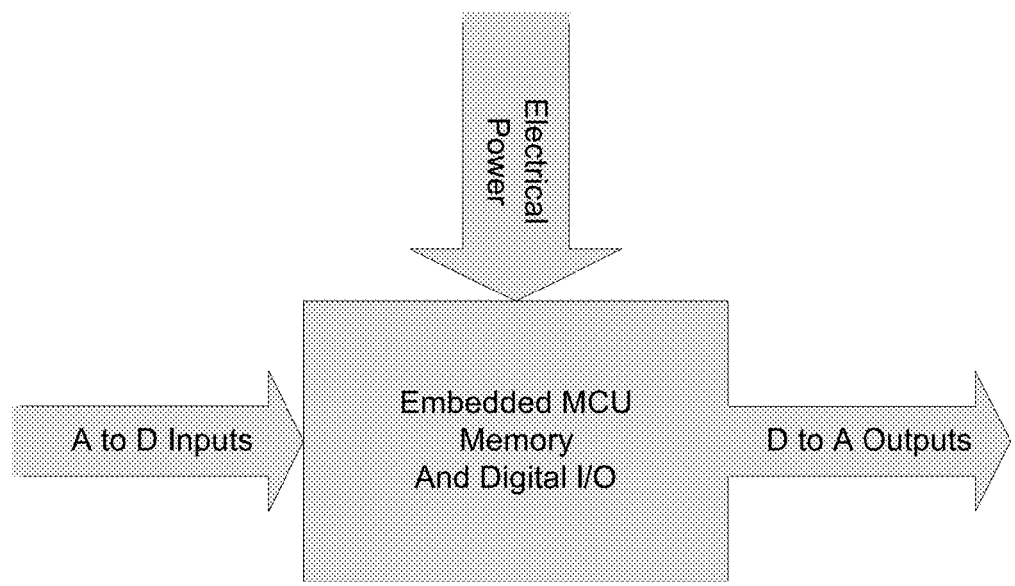
Figure 23:
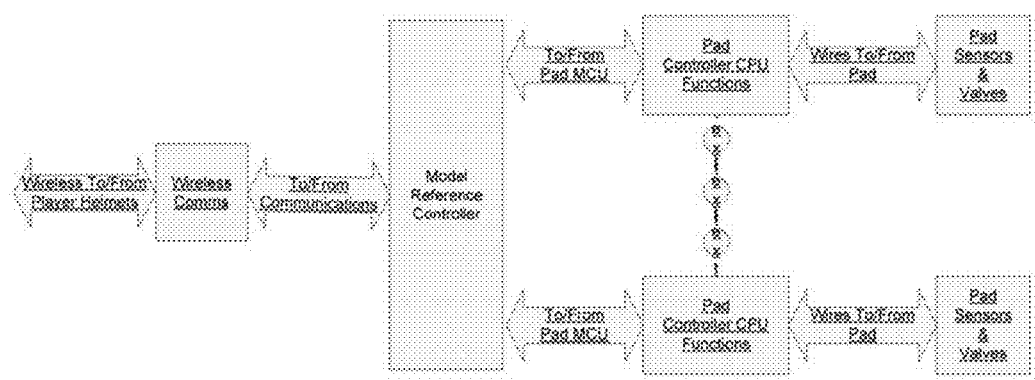

The Pressure Control Valves Sub-System Block Diagram (FIGS. 19A-19B) shown below has two major component sub-systems: Fluid Source Valve Controller Sub-System, and Fluid Sink Valve Controller Sub-System. Referring to FIG. 20 we illustrate the Pressure Control Valves Sub-System Block Diagram, which shows the multiple instances of the Pad pressure sensor sub-system (FIG. 21). Similarly, the Micro Computer Controller Sub-System Block Diagram (FIG. 22) has four major component sub-systems; Digital Input/Output Sub-System, Analog to Digital Converter Input Sub-System, Digital to Analog Converter Output Sub-System, and Embedded MCU with RAM/ROM/CPU, etc. Finally, the Wireless Communications Sub-System Block Diagram (FIG. 23) has five major component sub-systems; Helmet Wireless Transceiver with Auxiliary GPS Receiver, Sidelines Multi-Player Wireless Helmet Transceiver for Portable Computer, Sidelines Portable Computer, Sidelines Wireless Cellular Transceiver, and cellular-Connected Cloud Computing Database Server.

Figure 14:
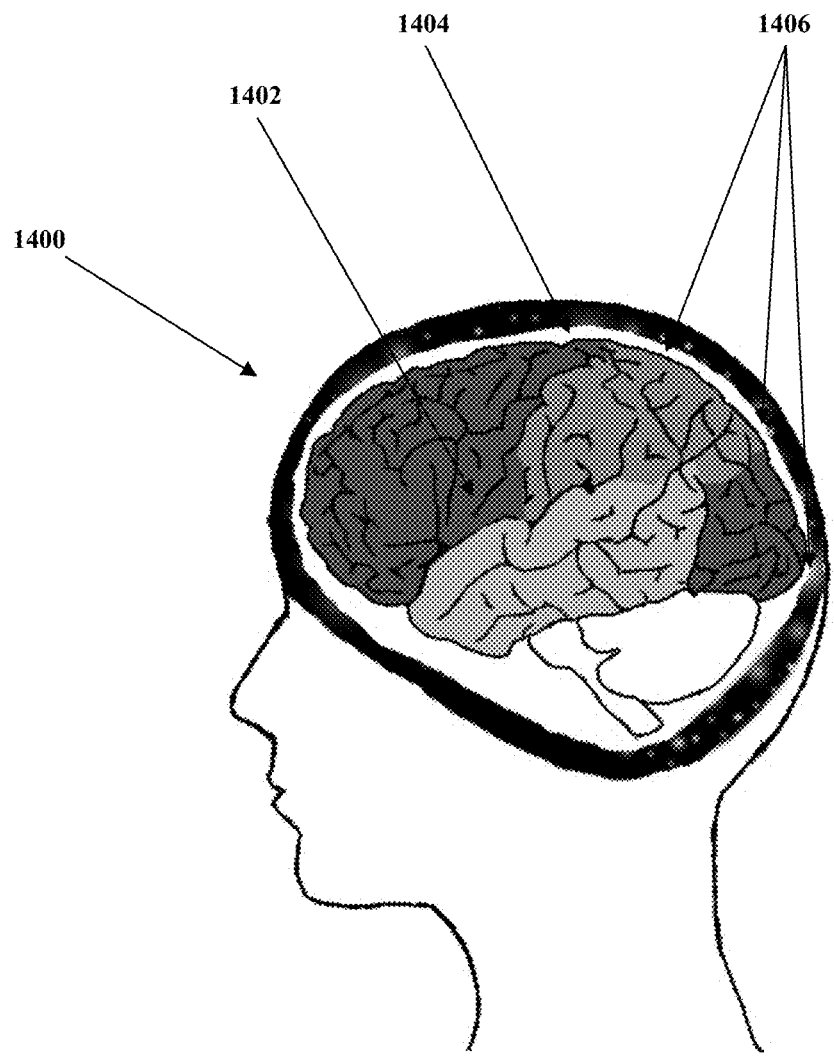
FIG. 14 shows an illustration of the human brain model, according to an exemplary embodiment of the invention.
Figure 15:
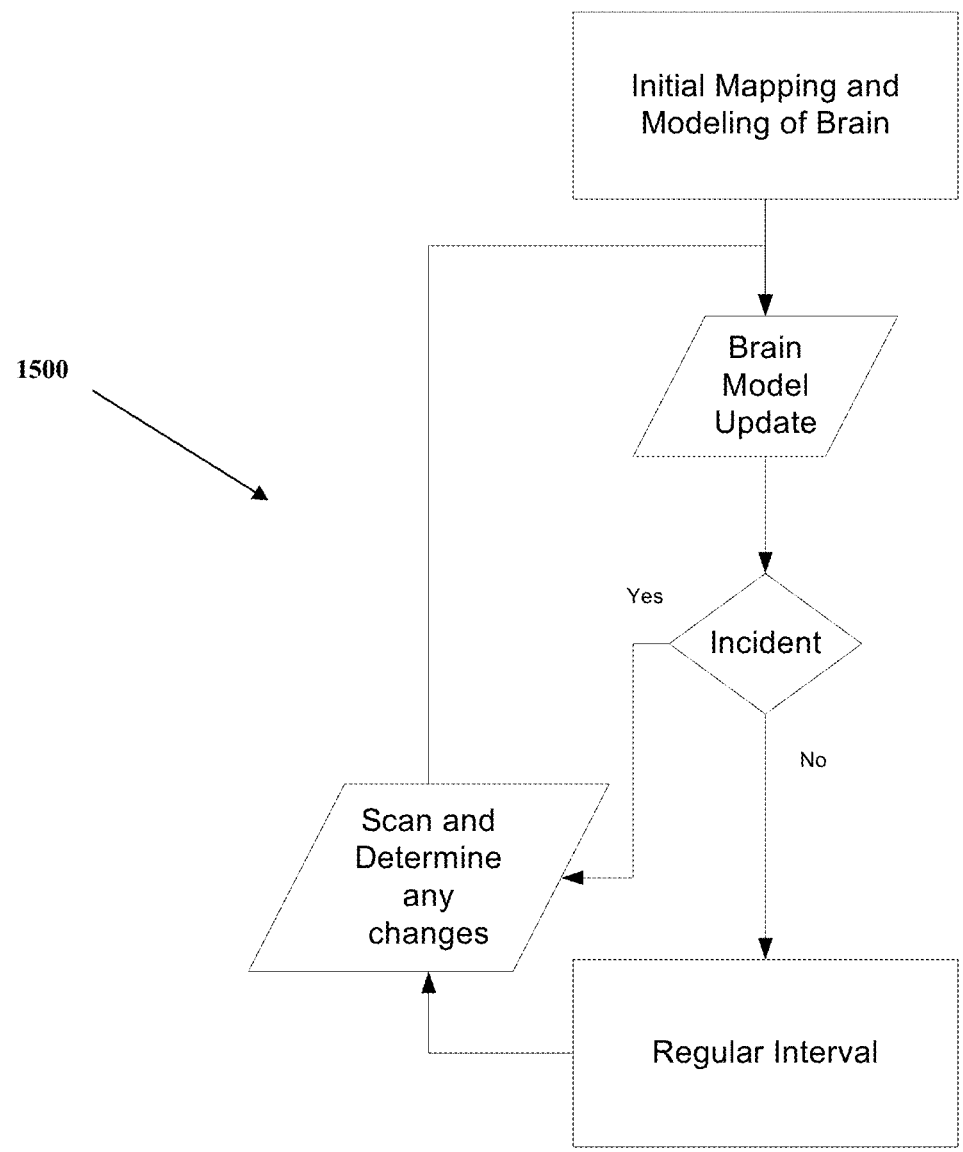
FIG. 15 shows an illustration of a proposed flowchart of the method, according to an exemplary embodiment of the invention.

Referring to FIGS. 14-15, we see a basic illustration of the human head 1400, including the brain 1402, the cranial cavity 1404, and the various vascular vessels 1406 which both connect the brain 1402 and provide it with fluids. The cranial cavity 1404 is usually full of cerebro-spinal craneo fluid, with keep the brain in a suspended state. The brain 1402 itself has the consistency of overcooked jello.

Preparing a model of the brain can then be accomplished using a 3D mesh that includes both a kinematic model of the various parts, as well as a computational fluid dynamic model of their interactions. In one embodiment 1500, a single patient has a model created using one or more of the scanning methodologies available, and their head or brain model is adjusted to account for the one or more discrepancies illustrated by the technologies, either at regular intervals or at times when an exceptional occurrence (such as an injury or accident) has occurred.

In an alternate embodiment, the telemetry or on-board recorded input data from a helmet or other piece of equipment (accelerometer in vehicle, ejection seat telemetry, fighter aircraft data, etc.) is used to provide subject's behavioral input in addition to any direct measurements. Over time, these input data elements are used to adjust one or more of the brain/head models of the subject.

The above data, both individually or that of groups or sub-groups (by ethnic group, age, sex, offensive/defensive line, Linebackers/Quarterbacks/Wide Receivers, etc.) is then used over time to provide improve the brain models. In such a fashion, professional sport entities (Leagues, teams, agents, players) could use the progressive updating of a player's head model to predict limits to behavior from an individual player, as well as analyzing the collective effects of new equipment/rules changes.

CONCLUSION

In concluding the detailed description, it should be noted that it would be obvious to those skilled in the art that many variations and modifications can be made to the preferred embodiment without substantially departing from the principles of the present invention. Also, such variations and modifications are intended to be included herein within the scope of the present invention as set forth in the appended claims. Further, in the claims hereafter, the structures, materials, acts and equivalents of all means or step-plus function elements are intended to include any structure, materials or acts for performing their cited functions.

It should be emphasized that the above-described embodiments of the present invention, particularly any "preferred embodiments" are merely possible examples of the implementations, merely set forth for a clear understanding of the principles of the invention. Any variations and modifications may be made to the above-described embodiments of the invention without departing substantially from the spirit of the principles of the invention. All such modifications and variations are intended to be included herein within the scope of the disclosure and present invention and protected by the following claims.

The present invention has been described in sufficient detail with a certain degree of particularity. The utilities thereof are appreciated by those skilled in the art. It is understood to those skilled in the art that the present disclosure of embodiments has been made by way of examples only and that numerous changes in the arrangement and combination of parts may be resorted without departing from the spirit and scope of the invention as claimed. Accordingly, the scope of the present invention is defined by the appended claims rather than the forgoing description of embodiments.

I claim:

1. An electronically actuated Micro-Electro-Mechanical Systems (MEMS) valve assembly for selectively opening or closing, said MEMS valve assembly comprising:

a semiconductor substrate sandwich having a first flat component having two or more openings going through said first component's body and second flat component located below said first component, said second component having two or more openings going through said second component, wherein said second component openings are located so that when said first and second components are placed in contact with each other there is no path through said combined first and second components, with two or more piezo-electric electric voltage actuated actuators located along the lateral edges of said first and second components and capable of moving said first and second components relative to each other so that a planar and non-bowing gap between said first and second components may be opened or closed through the coordinated operation of said piezo-electric actuators through movements of said first and second structural components away or towards each other.

* * * * *